United States Patent [19]

Mitsuhata et al.

[11] 4,389,338

[45] Jun. 21, 1983

[54] METHOD FOR MANUFACTURE OF SILVER CATALYST FOR PRODUCTION OF ETHYLENE OXIDE

[75] Inventors: Masashi Mitsuhata, Yokohama; Shin-ichi Nagase, Tokyo; Takahiko Nakai; Toshihiko Kumazawa, both of Yokohama, all of Japan

[73] Assignee: Nippon Skokubai Kagaku Kogyo Co., Ltd., Japan

[21] Appl. No.: 331,576

[22] Filed: Dec. 17, 1981

[30] Foreign Application Priority Data

Dec. 26, 1980 [JP] Japan .............................. 55-183935

[51] Int. Cl.³ ................... B01J 23/04; B01J 23/08; B01J 23/50
[52] U.S. Cl. ............................... 252/463; 252/476
[58] Field of Search .............................. 252/463, 476

[56] References Cited

U.S. PATENT DOCUMENTS 3,962,136  6/1976  Nielsen et al. ................ 252/476 X
4,033,903  7/1977  Maxwell ........................... 252/476
4,066,575  1/1978  Winnick ......................... 252/476 X
4,212,772  7/1980  Mross et al. ..................... 252/476
4,267,073  5/1981  Nielsen et al. ................. 252/476 X Primary Examiner—W. J. Shine
Attorney, Agent, or Firm—Omri M. Behr

[57] ABSTRACT

In a method for the manufacture of a silver catalyst having silver deposited on a porous inorganic carrier in conjunction with at least one reaction accelerator selected from the group consisting of alkali metals and thallium to be used for the production of ethylene oxide, the improvement comprising the steps of depositing silver on the porous inorganic carrier in conjunction with at least one reaction accelerator selected from the group consisting of alkali metals and thallium thereby preparing an activated silver catalyst and subsequently subjecting said silver catalyst to a high-temperature treatment at a temperature in the range of 550° to 950° C. in an inert gaseous atmosphere having an oxygen concentration of not more than 3 volume percent in the final step.

23 Claims, 3 Drawing Figures

METHOD FOR MANUFACTURE OF SILVER CATALYST FOR PRODUCTION OF ETHYLENE OXIDE

BACKGROUND OF THE INVENTION

1. Field of the Invention

This invention relates to a method for the manufacture of a silver catalyst to be used in the production of ethylene oxide by the catalytic vapor phase oxidation of ethylene with molecular oxygen.

2. Description of Prior Arts

It is universally known that virtually all catalysts to be used for the production, on a commercial scale, of ethylene oxide by the catalytic vapor phase oxidation of ethylene with molecular oxygen are silver-deposited catalyst having silver deposited on porous inorganic carriers. It is also a well-known fact that practically all these silver-deposited catalysts have promoters or so-called reaction accelerators deposited other than silver on the carriers for the purpose of acquiring high activity, high selectivity, and high durability as the performance demanded from the commercial point of view.

Although promoters or reaction accelerators sound very simple, they are widely varied. A review of patents which have issued to date in this field reveals that substantially all metallic elements appearing in the Periodic Table of Elements have been involved in some or others of such patents. It is only a small proportion of the numerous promoters or reaction accelerators so far developed that have found actual commercial adoption. Among others, alkali metals which have long been known well as reaction accelerators have recently come to attract increasing attention as evidenced by the great number of recent patent applications which, cover inventions involving the reaction accelerators. Examples are U.S. Pat. No. 3,962,136, U.S. Pat. No. 4,033,903 U.S. Pat. No. 4,066,575, U.S. Pat. No. 4,212,772 and U.S. Pat. No. 4,168,247. The catalysts offered by such inventions have more or less reached the level demanded from the commercial point of view and some of them demonstrate notable performance. Nevertheless, they still have room to be desired or improved. For example, the addition of alkali metals has entailed loss of activity in some inventions and the improvement of selectivity by the addition of alkali metals has fallen short of hitting the target in some other inventions. Particularly, the rapid loss of performance peculiar to alkali metal-deposited silver catalysts and the gradual loss of performance during storage are important problems which await solution.

To be more specific, use of alkali metals as reaction accelerators in silver catalysts for the production of ethylene oxide has a long history as described above. Use of sulfates of such alkali metals as potassium, rubidium and cesium already appeared in the specification of U.S. Pat. No. 2,671,764. Since then, alkali metal-deposited silver catalysts have often been disclosed in patent specifications. The catalysts as disclosed in such patent specifications represented technical achievements surpassing the technical levels prevailing at the respective times of relevant patent applications. Particularly, the catalyst disclosed by U.S. Pat. No. 3,962,136 deserves special attention in respect that, unlike the alkali metal-deposited silver catalysts developed therefore, it has fixed the amount of alkali metal to be added in a specific range and consequently succeeded in immensely improving the selectivity.

Many of the silver catalysts disclosed in the later patent specifications have had the amounts of alkali metal deposition and other various conditions limited with a view to providing improvements in catalyst performance. Catalysts possessed of fairly improved performance have come to appear.

Despite such notable improvements, these catalysts still have room for more selectivity and they are not quite free from the fault of the loss of capacity during use. Particularly the alkali metal-deposited silver catalysts, despite the notable initial improvement in selectivity due to the addition of alkalis, continue to suffer from the fault that the degradation of the performance occurs rapidly. For the catalysts which are expected to offer effective service for a number of years, such rapid loss of performance has a grave economic impact and remains to be an important problem awaiting a solution. When the alkali metal-deposited silver catalysts which have been activated are left standing unused for a prolonged period, say for half a year or one year, for the purpose of storage, for example, they have their activity and selectivity degraded during the standing. This gradual loss of performance can never be overlooked from the practical point of view.

For the explanation of these disadvantages, various factors are conceivable such as migration of alkali metal into silver or carrier, sintering of silver particles, change in chemical state of alkali metal, and poisoning of the catalyst during the use of the catalyst, and poisoning of the catalyst during the preservation. Yet, no definite proof is available for ascertaining the mechanism responsible for the loss of performance.

An object of this invention, therefore, is to provide a method for the manufacture of an improved silver catalyst for the production of ethylene oxide.

Another object of this invention is to provide a method for the manufacture of a silver catalyst of enhanced activity, selectivity, and durability for the production of ethylene oxide.

SUMMARY OF THE INVENTION

The objects described above are accomplished by this invention providing an improvement in and concerning a method for the manufacture of a silver catalyst formed of silver deposited in conjunction with at least one reaction accelerator selected from the group consisting of alkali metals and thallium on a porous inorganic carrier and used for the production of ethylene oxide, which improvement comprises preparing an activated silver catalyst having silver deposited on a porous inorganic carrier in conjunction with at least one reaction accelerator selected from the group consisting of alkali metals and thallium and finally treating the silver catalyst mentioned above in an inert gaseous atmosphere having an oxygen concentration of not more than 3 volume percent at a high temperature in the range of 550° to 950° C.

According to the present invention, the various faults found with the catalysts of the conventional techniques are eliminated and the selectivity is enhanced to an excellent level by the method which comprises the steps of depositing silver and at least one compound selected from the group consisting of alkali metals and thallium on a porous inorganic carrier, then heating the deposits and carrier thereby decomposing and activating the compounds supported on the carrier, and thereafter subjecting the deposits and carrier to a high-temperature treatment in an inert gaseous atmosphere having an oxygen concentration of not more than 3 volume percent at a high temperature in the range of 500° to 950° C.

DETAILED DESCRIPTION OF THE INVENTION

Figure 1:
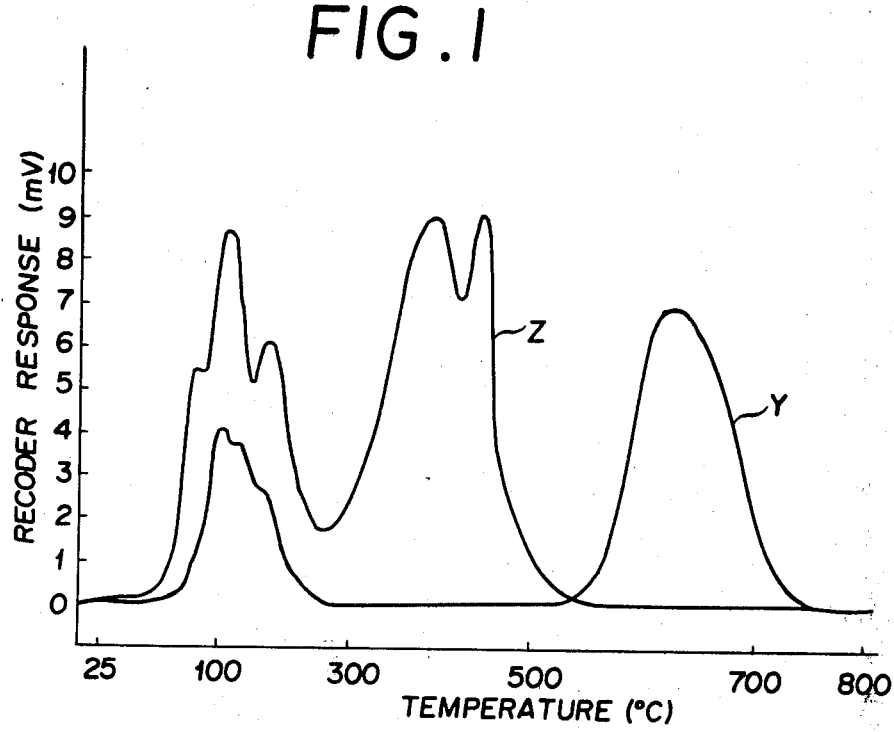
FIG. 1 is a chromatogram obtained by subjecting continuously to the temperature programmed desorption method the gas liberated when a silver catalyst activated without a high-temperature treatment was continuously heated in a gaseous atmosphere of helium at temperatures up to 700° C.

In the manufacture of the catalyst by the method of this invention, the portion of the procedure preceding a high-temperature treatment at the elevated temperature can be carried out by following the conventional method substantially in its unmodified form. The procedure which involves causing an aqueous solution or organic solvent solution of an organic or inorganic silver salt such as, for example, aqueous silver lactate solution or an organic amine solution of a silver salt of organic acid, and an aqueous solution or organic solvent solution of an alkali metal and/or thallium metal or compound such as, for example, aqueous cesium nitrate solution or an alcohol solution of cesium carbonate, to impregnate a porous inorganic carrier such as, for example, a carrier formed preponderantly of α-alumina, drying the carrier wet with the solutions mentioned above, elevating the temperature of the carrier thereby decomposing or reducing the silver salt, producing a carrier having the metal silver and the alkali metal and/or thallium or thallium compound deposited by precipitation thereon, and thereafter further elevating the temperature of the deposits supported on the carrier for effecting the so-called activation treatment which serves to provide thermal decomposition and expulsion of excess organic or inorganic components can be utilized, for example.

Virtually all the silver salt solutions heretofore known to the art can be used in this procedure. Among others, aqueous solutions of silver nitrate and silver lactate, amine solutions of silver oxalate, silver acetate, and silver carbonate, and a glycol solution of silver nitrate are used advantageously.

The catalyst should be prepared so that the ratio of silver deposited to the produced catalyst will fall in range of 5 to 25 weight percent, essentially 8 to 20 weight percent.

Virtually in all cases, the alkali metals and/or thallium are used in the form of organic salts or inorganic salts. For the sake of convenience, it is particularly desirable for them to be used in the form of water-soluble salts. Examples are nitrates, sulfates, hydroxides, oxides, and acetates, which are desired to be used as dissolved in water. Optionally, these compounds may be used as dissolved in lower alcohols such as methanol and ethanol.

The alkali metal to be used for the purpose of this invention is desired to be selected from the group consisting of potassium, rubidium, and cesium. In the group, cesium is the most desirable choice.

Optionally, a combination of two or more such alkali metals may be used.

The effective amount of the alkali metal to be deposited in the catalyst is in the range of 0.005 to 0.05 gram equivalent weight (gew), preferably 0.0085 to 0.03 gew, per kg of total catalyst. It should be noted that this amount does not include the amount of such alkali metals which find their way into the reaction system in the ordinary procedure of carrier manufacture or which are inadvertently or intentionally added to the reaction system during the manufacture of carrier. The effective amount of thallium to be deposited in the catalyst is in the range of 0.001 to 0.03 gew, preferably 0.002 to 0.02 gew, per kg of total catalyst. Even when two or more alkali metals and/or thallium are deposited on the carrier, their respective amounts should be limited within the ranges specified above.

In the procedure described above, effective manufacture of the catalyst can also be obtained by causing the alkali metal and/or thallium to be deposited on the carrier before the silver compound is deposited. Optionally, the alkali metal and/or thallium may be additionally deposited on the carrier after the step of activation. In this case, the deposits and the carrier are subjected to a high-temperature treatment at the elevated temperature after the alkali metal and/or thallium have been deposited by precipitation on the carrier.

All the porous inorganic carriers which are known to the art are usable for the purpose of this invention. Examples are porous refractory carriers using alumina, silica, silicon carbide, diatomaceous earth, zirconia, and magnesia. Particularly, a porous refractory carrier formed preponderantly of α-alumina is used advantageously. As regards the physical properties which the carriers are expected to possess, the specific surface area measured by the BET method is in the range of 0.1 to 5.0 $m^2/g$, preferably 0.2 to 3.0 $m^2/g$, and the apparent porosity is in the range of 25 to 70 percent, preferably 35 to 70 percent. The carrier to be used for this invention is a porous refractory inorganic carrier prepared in the form of particles such as pellets or rings. The average equivalent diameter of the particles is in the range of 3 to 20 mm, preferably 3 to 10 mm.

The activating treatment of this invention which is performed in this step can be carried out by following any of the ordinary methods adopted in this field. The method which effects thermal decomposition in air or in an inert gas at temperatures of about 150° to 400° C., which are more or less variable with the particular kinds of silver salt and solvent to be actually used, can be adopted. The thermal decomposition of an aqueous silver lactate solution or an amine solution of silver salt or organic acid is one example of the advantageous application of the method. The method which effects the activation by the reduction with the current of hydrogen is applicable where an aqueous silver nitrate is used as the source of silver. Besides, the method which effects the activation by the washing with water or a lower alcohol can be cited as a special case. This method can also be utilized for this invention. It should be noted, however, that where the method resorting to the washing technique is adopted, the deposition of the alkali metal and/or thallium should take place after the activation by the washing has been completed.

The silver catalyst containing the alkali metal and/or thallium which has undergone the activation described above is subjected to a high-temperature treatment at an elevated temperature in the range of 550° to 950° C. in an inert gaseous atmosphere having an oxygen concentration of not more than 3 volume percent, desirably not more than 1 volume percent, and preferably not more than 0.1 volume percent.

Examples of the inert gases which are effectively used in this step include nitrogen, helium, argon, carbon dioxide, and neon. In this group, preferred members are nitrogen, helium, are argon. Since nitrogen is inexpensive and easy to obtain, it is convenient to adopt nitrogen.

The temperature of the high-temperature treatment is in the range of 550° to 950° C., preferably 600° to 800° C.

The heating time must be at least 3 minutes. It is desired to fall in the range of 3 to 1440 minutes, preferably 20 to 900 minutes. The time required for elevating the temperature to the stated level and the time required for the temperature to fall from the heating temperature are not included in the heating time mentioned above. Generally, as will be noted from the working examples cited afterward, the duration of the high-temperature treatment may be short at relatively high temperatures and must be long at relatively low temperatures when the alkali metal and/or thallium are deposited in an equal amount.

It should be also noted that the silver catalyst of the present invention is effective when the amounts of alkali metal and/or thallium to be deposited therein are larger than the conventional levels.

In the silver catalyst containing an alkali metal and/or thallium which is produced without going through the high-temperature treatment at the elevated temperature as indispensably required for the method of this invention, the effective amounts of alkali metal and/or thallium are small. When a catalyst having alkali metal and/or thallium deposited in small amounts therein is subjected to a high-temperature treatment at an elevated temperature in an inert gas, the treatment brings about no advantageous effect and rather entails loss of performance below the level existing before the high-temperature treatment. This result of the high-temperature treatment just described may lead to an inference that the treatment causes the alkali metal and/or thallium to be scattered. However, the fact that the amounts of the alkali metal and/or thallium deposited in the catalyst show absolutely no change before and after the high-temperature treatment shows the inference to be wrong. Among other alkali metals, potassium, rubidium, and cesium give better results. Particularly, cesium produces the most desirable results.

The deposition of the alkali metal and/or thallium in the catalyst can be accomplished by a simple method available for this purpose comprises the steps of immersing the carrier for impregnation in an aqueous alkali metal compound solution and the silver solution, concentrating the solutions as containing the carrier, and drying the carrier impregnated with the solutions.

It is also important to note that the high-temperature treatment at the elevated temperature is not effective unless it is carried out in an inert gas having an oxygen concentration of not more than 3 volume percent, desirably not more than 1 volume percent, and preferably not more than 0.1 volume percent. When the high-temperature treatment at the elevated temperature is carried out in a gas having a high oxygen concentration fails to bring about any desirable result. The catalyst obtained in consequence of this treatment acquires performance inferior to the performance of the catalyst containing an alkali metal and/or thallium produced by the conventional method. This fact implies that in the high-temperature treatment at the elevated temperature involved in this invention, the oxygen concentration in the inert gas constitutes an important factor.

As will be noted from the working examples and the controls cited afterward, the magnitude of the oxygen concentration in the gas being used in the high-temperature treatment at the elevated temperature heavily affects the performance of the produced catalyst. One possible reason for this conspicuous effect of the oxygen concentration may be that, by a high-temperature treatment at the elevated temperature, the silver, alkali metal, and thallium is given some form of change ascribable to the particular condition of oxygen and consequently is fixed or cleaned.

Figure 2:
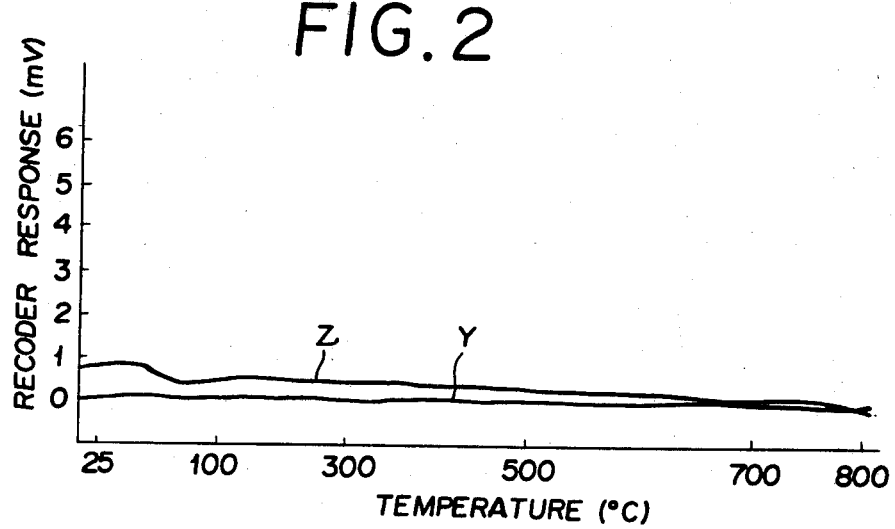
FIG. 2 is a chromatogram obtained by subjecting continuously to the temperature programmed desorption method the gas liberated when the catalyst of the present invention obtained by the high-temperature treatment was continuously heated in a gaseous atmosphere of helium at temperatures up to 700° C.

This proposition may be explained by reference to the chromatograms of FIG. 1 and FIG. 2 obtained by the temperature programmed desorption method. To be specific, FIG. 1 is a chromatogram obtained by subjecting continuously to the temperature programmed desorption method the gas liberated when a silver catalyst activated by the conventional method not involving the high-temperature treatment at the elevated temperature (Control 5) was continuously heated in an atmosphere of helium at temperatures up to 700° C. It is noted from FIG. 1 that the chromatogram of the gas obtained by the hydrogen flame ionization detector (FID) (curve W) and the chromatogram of the gas obtained by the thermal conductivity detector (TCD) (curve X) both indicate presence of some impure components in the gas. FIG. 2 is a chromatogram obtained by subjecting continuously to the temperature programmed desorption method the gas liberated when a catalyst of this invention resulting from the high-temperature treatment at the elevated temperature (Example 1) was heated in an atmosphere of helium gas at temperatures up to 700° C. It is noted from FIG. 2 that the chromatogram obtained by the FID (curve Y) and that obtained by the TCD (curve Z) are both flat and, therefore, imply perfect absence of impure components in the gas. This difference between the chromatograms of FIG. 1 and those of FIG. 2 is thought to be reflected to some extent in the difference of catalyst performance. The chromatograms shown in FIG. 1 are varied in shape depending on the method adopted for the manufacture of the catalyst. No matter what method there may be adopted, those peaks in the curves due to impure components appear unless the high-temperature treatment at the elevated-temperature is given to the catalyst.

The clear change which is discerned by the observation of the silver catalyst under scanning electron microscope is that of the size of silver particles in the catalyst before and after the catalyst is given the high-temperature treatment at the elevated temperature in a gas having a high oxygen concentration. This change will certainly result in the degradation of the activity of the catalyst. In the case of the catalyst manufactured by the method of this invention, virtually no change in the size of silver particles is observed before and after the high temperature treatment at the elevated temperature.

The strongest characteristic of this invention resides in giving to the deposits and carrier the high-temperature treatment at the elevated temperature in the final step of the manufacture of catalyst. The term "final" as used herein shall mean the interval between the time at which the so-called activation treatment, i.e. the thermal treatment performed in air or in an oxygen-containing gas at relatively low temperatures of 150° to 400° C., for example, for the purpose of decomposing and expelling organic substances and useless inorganic substances thereby conferring activity upon the silver compound and the reaction accelerator used in the preparation of the catalyst by the conventional method is completed and the time at which the produced catalyst is on the verge of undergoing degradation.

The study conducted by the inventors has ascertained that although the time at which a catalyst having silver and an alkali metal and/or thallium supported on a carrier begins to undergo degradation is variable from one kind of catalyst to another, the degradation becomes conspicuous after the age of the catalyst has passed more than six months. This means that the high-temperature treatment at the elevated temperature should be given during several months which follow the time of activation. Actually, with a view to avoiding unnecessary complication, however, it is desirable to conduct the high-temperature treatment either immediately after or only a short time after the completion of the activation.

The same rule applies when the activation has been carried out by some other method. If the high-temperature treatment at the elevated temperature is performed at a time not falling within the range of the final step, no effect can be expected of the treatment.

The "high-temperature" as used herein is clearly different from the temperature of the aforementioned activation treatment, i.e. the temperature of the order of 150° to 400° C. It shall mean a much higher temperature in the range of 500° to 950° C., preferably 600° to 800° C.

In literature there are disclosed activation treatments in which decomposition or reduction is carried out at extremely high temperatures of 400° to 800° C. for brief periods. These treatments, of course, differ clearly from the high-temperature treatment at the elevated temperature which is contemplated by the present invention. This because the high-temperature treatment at the elevated temperature in the method of this invention must not be carried out in an atmosphere having a high oxygen concentration as in air, namely because this high-temperature treatment at the elevated temperature, unlike the activation treatment, never brings about the same effect in air and in an inert gas. It is further because the high-temperature treatment must be carried out at high temperatures for long periods as at 700° C. for 30 minutes or at 600° C. for 720 minutes and because the alkali content in the produced catalyst is conspicuously high as compared with that in any of the catalysts obtained by the conventional methods. In terms of selectivity and durability among other catalyst performance, the catalyst obtained by the activation treatment at the elevated temperature is notably inferior to the catalyst obtained by the high-temperature treatment at the elevated temperature according to the present invention. This fact clearly indicates that the activation treatment is different from the high-temperature treatment conducted by this invention at the elevated temperature.

For the fixed amount of alkali metal and/or thallium and the fixed amount of silver deposited in the catalyst, the length of the high-temperature treatment at the elevated temperature may be short at relatively high temperatures and must be long at relatively low temperatures. This relationship of time and temperature is evident from Examples 5, 6 to be cited afterward.

Naturally the aforementioned characteristics of the present invention are never manifested when the requirement of the construction of invention that the silver catalyst having the alkali metal and/or thallium deposited in the amounts of 0.005 to 0.05 gew and 0.0001 to 0.03 gew per kg of total catalyst should be subjected, subsequently to the step of activation, to the high-temperature treatment at an elevated temperature of 550° to 950° C. in an inert gaseous atmosphere is not met in any respect or the sequence or procedure is not faithfully followed. Only when the activation is effected by washing silver or a silver compound with water or a lower alcohol, the high-temperature treatment at the elevated temperature should be performed exceptionally after the alkali metal and/or thallium have been deposited by precipitation on the carrier subsequently to the activation.

The effect of the present invention is not obtained when the high-temperature treatment is carried out in air, a gas containing oxygen in a high concentration, in the place of an inert gas, when the high-temperature treatment at the elevated temperature is carried out on a silver catalyst having an alkali metal and/or thallium deposited in amounts less than are specified or on a silver catalyst containing absolutely no alkali metal and/or thallium and consisting solely of silver, when the high-temperature treatment is carried out at a temperature lower than 550° C., or when the high-temperature treatment at the elevated temperature precedes the deposition of the alkali metal and/or thallium. This fact will become apparent from the review of Examples 1–6 and Controls 1–5 to be cited afterward.

In Control 1, the high-temperature treatment at the elevated temperature was performed in air, while in Example 1, the same treatment was performed in nitrogen. The results are shown in Table 1. In Control 2, the procedure of Example was followed, except that the addition of the aqueous cesium nitrate solution to the bath for the impregnation of the catalyst was made after completion of the high-temperature treatment at the elevated temperature. The results are also shown in Table 1. In Control 3, the procedure of Example 1 was followed, except that the amount of the alkali metal added was changed to the amount which would represent the highest possible content in the catalyst system having silver and the alkali metal deposited but for the high-temperature treatment at the elevated temperature and, after this addition the catalyst was subjected to the high-temperature treatment at the elevated temperature. The results are shown in Table 1. In Control 6, the catalyst obtained by the procedure of Control 3 excepting the high-temperature treatment at the elevated temperature was subjected to a prolonged test reaction. The results are compared with those of Example 14 in Table 2. The comparison clearly shows that the catalyst obtained by the method of this invention possesses outstanding durability.

Figure 3:
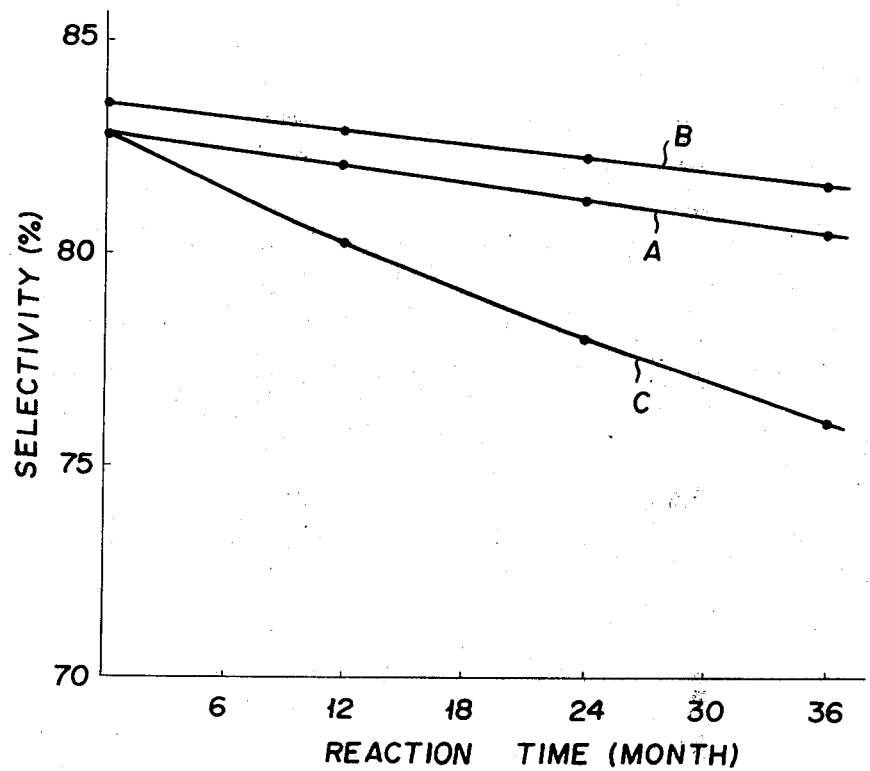
FIG. 3 is a graph showing the time-course changes of selectivity obtained of the silver catalyst produced by the present invention and the silver catalyst produced by the conventional method.

It is noted from FIG. 3 that the catalyst of Example 3 (curve A) and the catalyst of Example 14 (curve B) both showed very gradual time-course changes of selectivity. These results represent notable improvements over the results of the catalyst of Control 6 (curve C), an alkali metal-deposited silver catalyst by the conventional method. The comparison shows the decisive economic superiority of the catalyst of this invention.

In Control 7, the procedure of Control 3 was followed, except that the addition of the aqueous cesium nitrate solution was made after completion of the high-temperature treatment at the elevated temperature. The results are substantially the same as those of Control 6, indicating that the catalyst showed poor durability. In Control 8, the procedure of Control 6 was followed, except that the activation was carried out in nitrogen gas and the aqueous cesium nitrate solution was subsequently added and deposited on the carrier. The results are again substantially the same as those of Control 6, indicating that the catalyst showed poor durability.

In Control 9, the procedure of Control 3 was followed, except that the catalyst not yet subjected to the high-temperature treatment at the elevated temperature was preserved unused in a polyethylene bag for 12 months. The results of reaction obtained with this catalyst are compared with those of Example 15 in Table 2. The comparison shows that the catalyst obtained by the method of this invention excels the catalyst of Control 9 in preservability.

The conditions which can be adopted for the production of ethylene oxide by the oxidation of ethylene with molecular oxygen in the presence of the silver catalyst prepared by the method described above are those which have heretofore been invariably known in the art. The general conditions involved in the commercial production of ethylene oxide, namely a feed gas composition consisting of 0.5 to 40% by volume of ethylene, 3 to 10% by volume of oxygen, 5 to 30% by volume of carbon dioxide and the balance to make up 100% by volume of other compounds including an inert gas such as nitrogen, argon or steam, a lower hydrocarbon such as methane or ethane and 0.1 to 10 ppm of a halide such as ethylene dichloride or diphenyl chloride which serves the part of a reaction inhibitor, a space velocity of the feed gas filling within the range of from 3,000 to 10,000 hr$^{-1}$ (S.T.P.) and a pressure within the range of from 2 to 40 kg/cm$^2$ (gauge pressure) can be advantageously adopted.

Now, the present invention will be described more specifically with reference to working examples and controls. The present invention, illustrated and not limited in any way by these working examples, may be allowed modifications and alterations without departing from the spirit thereof.

The numerical values of conversion and selectivity indicated in whole specification including the working examples and controls experiments which follow have been calculated in accordance with the following formulas.

$$\text{Conversion (\%)} = \frac{\text{Moles of ethylene converted}}{\text{Moles of ethylene fed}} \times 100$$

$$\text{Selectivity (\%)} = \frac{\text{Moles of ethylene oxide formed}}{\text{Moles of ethylene converted}} \times 100$$

Example 1

Silver oxalate weighing 830 g was mixed with 200 ml of water to afford a pasty mixture. This pasty mixture was kept cooled and 700 ml of monoethanol amine was added thereto and stirred thoroughly therewith until solution. With the resultant solution, a solution obtained by dissolving 10.7 g of cesium nitrate in 200 ml of water was thoroughly stirred. In the resultant mixture, 4000 ml of α-alumina carrier having an apparent porosity of 56 percent and a specific surface area of 1.2 m$^2$/g and heated in advance to about 100° C. was immersed to be impregnated. The mixture and the carrier combined were concentrated and dried by heating, then further heated in an air bath at 120° C. for three hours, and thereafter activated in a current of air at 260° C. for 24 hours.

The catalyst thus obtained was packed in a closed container of stainless steel adapted to admit an inert gas supplied from an outside source. Under continued supply of nitrogen gas in an electric furnace, the catalyst bed as held in the container was subjected to a high-temperature treatment by heating at 700° C. for 30 minutes.

The catalyst was packed in an external heating type double tube reactor of stainless steel having an inside diameter of 25 mm and a tube length of 11000 mm. To the packed bed of the catalyst, a mixed gas consisting of 20 volume percent of ethylene, 8 volume percent of oxygen, 7 volume percent of carbon dioxide, the balance to make up 100 volume percent of methane, nitrogen, argon, and ethane and additionally entraining 1 ppm of ethylene dichloride was introduced to induce reaction, with the reaction pressure fixed at 24 kg/cm$^2$ (gauge pressure), the space velocity at 5,500 hr$^{-1}$, and the temperature of the heat medium elevated to 211° C. The results are shown in Table 1.

Examples 2-11

Catalysts were prepared by following the procedure of Example 1, except that the conditions were varied as shown in Table 1. The reactions using the catalysts were carried out under the same conditons as those of Example 1, except that the temperature of the heat medium was varied as indicated. The results are shown in Table 1.

Control 1

The procedure of Example 1 was repeated, except that the high-temperature treatment at the elevated temperature was carried out in air instead of in nitrogen gas. The results of the reaction using the resultant catalyst are shown in Table 1.

Control 2

The procedure of Example 1 was repeated, except that the addition of the aqueous cesium nitrate solution was made after the catalyst had undergone the high-temperature treatment as the elevated temperature. The results of the reaction using the resultant catalyst are shown in Table 1.

Control 3

The procedure of Example 1 was repeated, except that the amount of cesium nitrate was varied as indicated in Table 1. The results of the reaction using the resultant catalyst are shown in Table 1.

Control 4

The procedure of Example 1 was repeated, except that the temperature of the high-temperature treatment was change to 400° C. The results of the reaction using the resultant catalyst are shown in Table 1.

Control 5

The procedure of Example 1 was repeated, except that the high-temperature treatment at the elevated temperature was totally omitted. The results of the reaction using the resultant catalyst are shown in Table 1.

for three hours, and then activated in a current of air at 240° C. for 24 hours.

The resultant catalyst was subjected to the same high-temperature treatment at the elevated temperature as that of Example 1. The catalyst was then subjected to the same reaction as involved in Example 1. The reaction temperature was 226° C., the conversion 7.5 percent, and the selectivity 81.1 percent.

TABLE 1

| | Porous inorganic carrier | | Alkali metal and/or thallium | | Silver content | High-temperature treatment at elevated temperature | | |
|---|---|---|---|---|---|---|---|---|
| | Apparent porosity (%) | Specific surface area (m²/g) | Compound | Gew per kg of total catalyst | (% by weight) | Kind of ambient gas | Temperature of heating (°C.) | Time of heating (min.) |
| Example | | | | | | | | |
| 1 | 56 | 1.2 | $CsNO_3$ | 0.0116 | 12.5 | nitrogen | 700 | 30 |
| 2 | 56 | 1.2 | $CsNO_3$ | 0.0116 | 12.5 | argon | 700 | 30 |
| 3 | 57 | 0.34 | $CsNO_3$ | 0.0087 | 12.5 | helium | 700 | 30 |
| 4 | 57 | 0.34 | $CsNO_3$ | 0.0087 | 12.5 | 1.0 vol % $O_2$ contng. helium | 700 | 30 |
| 5 | 57 | 0.34 | $CsNO_3$ | 0.0087 | 12.5 | helium | 600 | 720 |
| 6 | 56 | 1.2 | $CsNO_3$ | 0.0116 | 12.5 | helium | 800 | 5 |
| 7 | 56 | 1.2 | $Rb_2SO_4$ | 0.0257 | 12.5 | nitrogen | 700 | 30 |
| 8 | 57 | 0.34 | $KNO_3$ | 0.0198 | 12.5 | nitrogen | 700 | 30 |
| 9 | 60 | 2.6 | $CsNO_3$ | 0.0300 | 12.5 | nitrogen | 700 | 30 |
| 10 | 57 | 0.34 | $TlNO_3$ | 0.0041 | 12.5 | helium | 700 | 30 |
| 11 | 56 | 1.2 | $TlNO_3$ | 0.0104 | 12.5 | helium | 600 | 720 |
| Control | | | | | | | | |
| 1 | 56 | 1.2 | $CsNO_3$ | 0.0116 | 12.5 | air | 700 | 30 |
| 2 | 56 | 1.2 | $CsNO_3$ | 0.0116 | 12.5 | nitrogen | 700 | 30 |
| 3 | 56 | 1.2 | $CsNO_3$ | 0.0044 | 12.5 | nitrogen | 700 | 30 |
| 4 | 56 | 1.2 | $CsNO_3$ | 0.0116 | 12.5 | nitrogen | 400 | 30 |
| 5 | 56 | 1.2 | $CsNO_3$ | 0.0116 | 12.5 | — | — | — |

| | Results of reaction | | | |
|---|---|---|---|---|
| | Temperature of reaction (°C.) | Conversion (%) | Selectivity (%) | Remark |
| Example | | | | |
| 1 | 211 | 7.5 | 83.4 | |
| 2 | 212 | 7.5 | 83.3 | |
| 3 | 222 | 7.5 | 82.7 | |
| 4 | 225 | 7.5 | 81.2 | |
| 5 | 220 | 7.5 | 82.2 | |
| 6 | 218 | 7.5 | 81.9 | |
| 7 | 223 | 7.5 | 79.9 | |
| 8 | 235 | 7.5 | 78.3 | |
| 9 | 207 | 7.5 | 80.4 | |
| 10 | 220 | 7.5 | 79.6 | |
| 11 | 209 | 7.5 | 79.9 | |
| Control | | | | |
| 1 | 229 | 7.5 | 77.1 | High-temperature treatment performed in air. |
| 2 | 265 | — | almost not reacted | Addition of $CsNO_3$ made after high temperature treatment. |
| 3 | 202 | 7.5 | 77.4 | Amount of alkali metal for deposition decreased. |
| 4 | 265 | — | almost not reacted | Temperature of high temperature treatment lowered. |
| 5 | 265 | — | almost not reacted | High temperature treatment totally omitted. |

(Note)
Purity of ambient gas used for high temperature treatment
(1) In Examples 1, 7, 8 and 9 and Controls 2, 3, and 4, nitrogen containing 0.1 volume percent of oxygen was used.
(2) In Example 2, argon having a purity of 99.99 volume percent was used.
(3) In Example 3, 5, 6, 10, and 11, helium having a purity of 99.99 volume percent was used.
gew: gram equivalent weight

Example 12

A silver lactate paste formed by mixing 800 g of silver lactate with 1,100 g of water was converted into a solution by heating. This solution and a solution obtained by dissolving 6.9 g of cesium sulfate in 100 ml of water were thoroughly stirred and simultaneously concentrated to a total volume of about 1200 ml. In the resultant concentrated solution, 4,000 ml of α-alumina carrier having an apparent porosity of 57 percent and a specific surface area of 0.34 m²/g and heated in advance to 100° to 120° C. was immersed and impregnated. The solution containing the carrier was concentrated and dried by heating, burnt in an air bath at 130° to 180° C.

Example 13

Silver nitrate weighing 725 g was dissolved in 1,100 g of monoethylene glycol. The resultant solution was thoroughly mixed with 290 g of formamide added thereto. In the mixed solution, 4,000 ml of α-alumina carrier having an apparent porosity of 56 percent and a specific surface are of 1.2 m²/g and heated in advance was immersed and, under continued agitation, heated at 120° to 130° C. for two hours, and further at 150° to 160° C. for two hours. The resultant catalyst was washed by being boiled three times in 3000 ml of water and then dried.

The catalyst was immersed in a solution obtained by dissolving 9.7 g cesium carbonate in 1500 ml of ethyl alcohol. The catalyst in the solution was stirred and heated so as to be dried by evaporation.

The resultant catalyst was subjected to the high-temperature treatment at the elevated temperature as in Example 1. It was then subjected to the same reaction as involved in Example 1. The reaction temperature was 217° C., the conversion 7.5 percent, and the selectivity 83.1 percent.

Example 14–15

Catalysts were prepared by faithfully following the procedure of Example 1, and the catalysts were subjected to the high-temperature treatment at the elevated temperature as in Example 1. The catalyst of Example 14 was subjected to the same reaction as in Example 1. The catalyst of Example 15 was preserved in a polyethylene bag for 12 months and, after the storage, subjected to the same reaction as in Example 1. The results are shown in Table 2.

Control 6

The procedure of Control 3 was repeated, except that the produced catalyst was not subjected to the high-temperature treatment at the elevated temperature. The catalyst was subjected to the same reaction as involved in Example 1. The results are shown in Table 2.

Control 7

The procedure of Control 3 was repeated, except that the addition and deposition of cesium nitrate was carried out after completion of the high-temperature treatment at the elevated temperature. The results of the reaction using the catalyst are shown in Table 2.

Control 8

The procedure of Control 6 was repeated, except that the activation treatment was carried out in nitrogen gas and the addition and deposition of cesium nitrate was carried out after the activation treatment. The results are shown in Table 2.

Control 9

The procedure of Control 6 was repeated, except that the catalyst produced was preserved in a polyethylene bag for 12 months and, after the storage, subjected to the same reaction as in Example 1. The results are shown in Table 2.

TABLE 2

| | Porous inorganic carrier | | Alkali metal and/or thallium | | Silver content (% by weight) | High-temperature treatment at elevated temperature | | |
|---|---|---|---|---|---|---|---|---|
| | Apparent porosity (%) | Specific surface area (m²/g) | Compound | gew per kg of total catalyst | | Kind of ambient | Temperature of heating (°C.) | Time of heating (min.) |
| Example | | | | | | | | |
| 14 | 56 | 1.2 | CsNO₃ | 0.0116 | 12.5 | nitrogen | 700 | 30 |
| 15 | 56 | 1.2 | CsNO₃ | 0.0116 | 12.5 | nitrogen | 700 | 30 |
| Control | | | | | | | | |
| 6 | 56 | 1.2 | CsNO₃ | 0.0044 | 12.5 | — | — | — |
| 7 | 56 | 1.2 | CsNO₃ | 0.0044 | 12.5 | nitrogen | 700 | 30 |
| 8 | 56 | 1.2 | CsNO₃ | 0.0044 | 12.5 | — | — | — |
| 9 | 56 | 1.2 | CsNO₃ | 0.0044 | 12.5 | — | — | — |

| | Result of 30 days' reaction | | | Results of one year's reaction | | | |
|---|---|---|---|---|---|---|---|
| | Temperature of reaction (°C.) | Conversion (%) | Selectivity (%) | Temperature of reaction (°C.) | Conversion (%) | Selectivity (%) | Remark |
| Example | | | | | | | |
| 14 | 211 | 7.5 | 83.4 | 215 | 7.5 | 82.9 | |
| 15 | 213 | 7.5 | 83.2 | — | — | — | Reaction performed after 12 month's preservation. |
| Control | | | | | | | |
| 6 | 219 | 7.5 | 82.7 | 226 | 7.5 | 80.3 | |
| 7 | 220 | 7.5 | 82.2 | 228 | 7.5 | 80.0 | Addition of CsNO₃ made after high temperature treatment. |
| 8 | 223 | 7.5 | 81.5 | 231 | 7.5 | 79.0 | CsNO₃ added after activation performed in nitrogen gas. |
| 9 | 228 | 7.5 | 80.1 | — | — | — | Reaction performed after 12 months' preservation. |

(Note)
Purity of ambient gas used for high-temperature treatment
In Examples 14, 15, and Control 7, nitrogen containing 0.1 volume percent of oxygen was used.

Example 16

A catalyst was prepared by following the procedure of Example 1. This catalyst was subjected to the reaction by following the procedure of Example 1, except that the ethylene content was changed to 30 volume percent and the ethylene dichloride content to 1.7 ppm, the space velocity was fixed at 6,600 hr⁻¹ and the temperature of the heat medium at 226° C. The conversion was 5 percent and the selectivity was 80.7 percent.

Example 17

A catalyst was prepared by following the procedure of Example 1. The catalyst was subjected to the reaction by following the procedure of Example 1, except that the ethylene content was changed to 15 volume percent and the ethylene dichloride content to 0.5 ppm, the conversion to 10 percent, and the temperature of the heat medium to 212° C. The selectivity was 81.8 percent.

What is claimed is:

1. In a method for the manufacture of a silver catalyst having silver deposited on a porous inorganic carrier in conjunction with at least one reaction accelerator selected from the group consisting of alkali metals and thallium to be used for the production of ethyelene oxide, the improvement comprising the steps of depositing silver on the porous inorganic carrier in conjunction with at least one reaction accelerator selected from the group consisting of alkali metals and thallium thereby preparing an activated silver catalyst and subsequently subjecting said silver catalyst to a high-temperature treatment at a temperature in the range of 550° to 950° C. in an inert gaseous atmosphere having an oxygen concentration of not more than 3 volume percent in the final step.

2. A method according to claim 1, wherein the oxygen concentration in the inert gas is not more than 1 volume percent.

3. A method according to claim 1, wherein the oxygen concentration in the inert gas is not more than 0.1 volume percent.

4. A method according to claim 1, wherein the inert gas is at least one member selected from the group consisting of nitrogen, carbon dioxide, helium, argon, and neon.

5. A method according to claim 1, wherein the inert gas is at least one member selected from the group consisting of nitrogen, helium, and argon.

6. A method according to claim 1, wherein the high-temperature treatment is carried out at an elevated temperature in the range of 600° to 800° C.

7. A method according to claim 1, wherein the high-temperature treatment is carried out for at least three minutes.

8. A method according to claim 6, wherein the high-temperature treatment is carried out for a period in the range of 3 to 1440 minutes.

9. A method according to claim 6, wherein the high-temperature treatment is carried out for a period in the range of 20 to 900 minutes.

10. A method according to claim 1, wherein the amount of silver deposited in the catalyst is in the range of 5 to 25 weight percent based on the total catalyst.

11. A method according to claim 1, wherein the porous inorganic carrier has a specific surface area in the range of 0.1 to 5 $m^2$/g.

12. A method according to claim 1, wherein the porous inorganic carrier has a specific surface area in the range of 0.2 to 3 $m^2$/g.

13. A method according to claim 1, wherein the silver and the reaction accelerator are added and deposited on the porous inorganic carrier at the same time.

14. A method according to claim 1, wherein the reaction accelerator is added and deposited on the porous inorganic carrier before the deposition of the silver.

15. A method according to claim 1, wherein the reaction accelerator is added and deposited on the porous inorganic carrier after the deposition of the silver by precipitation.

16. A method according to claim 1, wherein the reaction accelerator is an alkali metal.

17. A method according to claim 16, wherein the alkali metal is at least one member selected from the group consisting of potassium, rubidium, and cesium.

18. A method according to claim 16, wherein the alkali metal is cesium.

19. A method according to claim 16, wherein the amount of the alkali metal deposited is in the range of 0.005 to 0.05 gram equivalent weight per kg of total catalyst.

20. A method according to claim 16, wherein the amount of the alkali metal deposited is in the range of 0.0085 to 0.03 gram equivalent weight per kg of total catalyst.

21. A method according to claim 1, wherein the reaction accelerator is thallium.

22. A method according to claim 21, wherein the amount of thallium deposited is in the range of 0.001 to 0.03 gram equivalent weight per kg of total catalyst.

23. A method according to claim 21, wherein the amount of thallium deposited is in the range of 0.002 to 0.02 gram equivalent weight per kg of total catalyst.

* * * * *